(12) United States Patent
Nishiyama et al.

(10) Patent No.: US 6,573,399 B1
(45) Date of Patent: Jun. 3, 2003

(54) SYNTHESIS OF α-AMINO-α', α'-DIHALOKETONES AND PROCESS FOR THE PREPARATION OF β-AMINO ACID DERIVATIVES BY THE USE OF THE SAME

(75) Inventors: Akira Nishiyama, Kakogawa (JP); Kenji Inoue, Kakogawa (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/700,207

(22) PCT Filed: Mar. 9, 2000

(86) PCT No.: PCT/JP00/01424
§ 371 (c)(1),
(2), (4) Date: Feb. 21, 2001

(87) PCT Pub. No.: WO00/53575
PCT Pub. Date: Sep. 14, 2000

(30) Foreign Application Priority Data

Mar. 10, 1999 (JP) .............................. 11/063478

(51) Int. Cl.⁷ ............................... C07C 26/00
(52) U.S. Cl. .............................. 560/24; 560/29; 560/38; 564/337; 564/342; 564/463; 564/502
(58) Field of Search ................. 568/305, 306, 568/307, 382, 308; 560/24, 29, 38; 564/337, 342, 463, 502

(56) References Cited

U.S. PATENT DOCUMENTS 6,150,567 A    11/2000   Sugawa et al.

FOREIGN PATENT DOCUMENTS

| WO | WO 98/07687 | * 2/1998 | ......... C07C/229/22 |
| WO | WO97/28105 | 3/1998 | |

OTHER PUBLICATIONS

José Barluenga et al, "The First Direct Preparation of Chiral Functionalised Ketones and Their Synthetic Uses", J. Chem. Soc., Chem. Comm., (1994), pp. 969–970.*

* cited by examiner

*Primary Examiner*—Paul J. Killos
(74) *Attorney, Agent, or Firm*—Connolly Bove Lodge & Hutz LLP

(57) ABSTRACT

The present invention provides a commercially profitable process for producing a β-amino acid ester derivative
   which comprises reacting an α-amino acid ester derivative with a base and a dihalomethane,
   reacting the same with a lithium amide and an alkyllithium in succession,
   and treating the reaction product with an acid in an alcohol.

7 Claims, No Drawings

SYNTHESIS OF α-AMINO-α', α'-DIHALOKETONES AND PROCESS FOR THE PREPARATION OF β-AMINO ACID DERIVATIVES BY THE USE OF THE SAME

TECHNICAL FIELD

The present invention relates to a process for producing a β-amino acid ester derivative of value as intermediates of pharmaceutical and agrochemical substances, particularly an optically active β-amino acid ester derivative, and to a process for producing an α-amino-α',α'-dihaloketone derivative of value as its intermediates.

BACKGROUND ART

As the standard method of producing β-amino acids from α-amino acids, the process which comprises reacting a mixed acid anhydride of an α-amino acid with diazomethane and causing the resulting α-amino-α'-diazoketone to undergo rearrangement in an alcohol in the presence of a metal catalyst such as silver ion (Liebigs Ann, 1995, pp.1217–122) is known. However, this process requires the use of diazomethane, an explosive and highly toxic substance, for synthesizing said α-amino-α'-diazoketone so that it is unsuited for a commercial operation.

As an alternative technology, there is known a process which comprises reducing an a-amino acid ester derivative with sodium borohydride, mesylating the resulting alcohol, reacting the mesylate with sodium cyanide, and hydrolyzing the resulting nitrile (Org. Prep Proced Int. 1994, 26(5), 599). However, this process involves many reaction steps and, in addition, requires the use of the highly toxic cyanide, thus being not suited for commercial exploitation.

In the above state of the art, the present invention has for its object to provide a commercially profitable process for synthesizing optically active β-amino acid ester derivatives of value in the pharmaceutical and other fields, starting with readily available optically active α-amino acid esters.

DISCLOSURE OF THE INVENTION

Thus, the present invention is directed to a process for producing a β-amino acid ester derivative of the following formula (4):

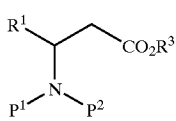
(4)

wherein $R^1$ represents a substituted or unsubstituted alkyl group containing 1 to 18 carbon atoms, an aralkyl group containing 7 to 18 carbon atoms or an aryl group containing 6 to 18 carbon atoms, $R^3$ represents an alkyl group containing 1 to 5 carbon atoms, and $P^1$ and $P^2$ each independently represents a hydrogen atom or an amino-protecting group or $P^1$ and $P^2$ taken together represents a phthaloyl group, excluding the case in which both $P^1$ and $P^2$ are hydrogen atoms, which comprises reacting an α-amino acid ester derivative of the following formula (1):

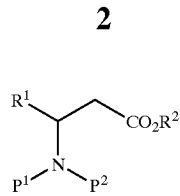
(1)

wherein $R^1$, $P^1$ and $P^2$ are as respectively defined above, $R^2$ represents an alkyl group containing 1 to 5 carbon atoms or an aralkyl group containing 7 to 12 carbon atoms, with a base and a dihalomethane of the following formula (2):

$$CH_2X^1X^2 \quad (2)$$

wherein $X^1$ and $X^2$ each independently represents a halogen atom, to synthesize an α-amino-α',α'-dihaloketone derivative of the following formula (3):

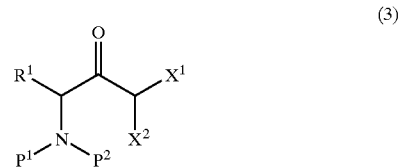
(3)

wherein $R^1$, $P^1$, $P^2$, $X^1$ and $X^2$ are as respectively defined above, reacting this derivative with a lithium amide and an alkyllithium in succession, and treating the reaction product with an acid in an alcohol.

The present invention is further directed to a process for producing an α-amino-α',α'-dihaloketone derivative of the above general formula (3) which comprises reacting an α-amino acid ester derivative of the above formula (1) with a base and a dihalomethane of the above formula (2).

In another aspect, the present invention is directed to a process for producing a β-amino acid ester derivative of the above formula (4) which comprises reacting an α-amino-α',α'-dihaloketone derivative of the above formula (3) with a lithium amide and an alkyllithium in succession, and treating the reaction product with an acid in an alcohol.

In a still another aspect, the present invention is directed to an α-amino-α',α'-dihaloketone derivative of the above formula (3) wherein $R^1$ is a benzyl group, $X^1$ is a bromine atom, $X^2$ is a chlorine atom or a bromine atom.

The present invention is now described in detail.

Referring to the above formulas (1), (3) and (4), $R^1$ represents a substituted or unsubstituted straight-chain, branched-chain or cyclic alkyl group containing 1 to 18 carbon atoms, an aralkyl group containing 7 to 18 carbon atoms, or an aryl group containing 6 to 18 carbon atoms. As specific examples, there can be mentioned benzyl, methyl, isopropyl, isobutyl, sec-butyl and phenyl, although these are not exclusive choices. Preferred is benzyl or phenyl.

Referring to the formula (1), $R^2$ represents an alkyl group containing 1 to 5 carbon atoms or an aralkyl group containing 7 to 12 carbon atoms. As specific examples, there can be mentioned methyl, ethyl, n-propyl, isopropyl, n-butyl, isobutyl, sec-butyl, benzyl, p-methylbenzyl, p-methoxybenzyl, p-nitrobenzyl and p-chlorobenzyl, among others. Preferred is methyl or ethyl.

In the formulas (1), (3) and (4), $P^1$ and $P^2$ each independently represents a hydrogen atom or an amino-protecting group, or $P^1$ and $P^2$ taken together represents a phthaloyl group; excluding the case in which both $P^1$ and $P^2$ are hydrogen atoms.

The amino-protecting group is not particularly restricted as far as it is a protecting group in routine use for the protection of an amino group. Thus, the groups mentioned in Protective Groups in Organic Synthesis, 2nd Ed., Theodora W. Green, John Willey & Sons), 1990, pp.309–384, e.g. methyloxycarbonyl, ethyloxycarbonyl, benzyloxycarbonyl, t-butyloxycarbonyl, acetyl, trifluoroacetyl, benzyl, dibenzyl, phthalimido, tosyl, benzoyl, trimethylsilyl, etc., can be employed. Preferred, among these, are carbamate-form protecting groups such as, for example, methyloxycarbonyl, ethyloxycarbonyl, benzyloxycarbonyl and t-butyloxycarbonyl. When either one of $P^1$ and $P^2$ represents an amino-protecting group, the other preferably represents a hydrogen atom. When $P^1$ and $P^2$ taken together represents a phthaloyl group, it may also be regarded as a kind of amino-protecting group.

$X^1$ and $X^2$ in the formulas (2) and (3) each independently represents a halogen atom, i.e. a fluorine, chlorine, bromine or iodine atom. Preferred is a chlorine atom or a bromine atom. $X^1$ and $X^2$ may be the same or different.

$R^3$ in the formula (4) represents a straight-chain or branched-chain alkyl group containing 1 to 5 carbon atoms. Preferred is methyl, ethyl, n-propyl or the like.

The process for producing an α-amino-α',α'-dihaloketone derivative in accordance with the present invention is now described.

Thus, an α-amino acid ester derivative of the formula (1) is reacted with a base and a dihalomethane of the formula (2) at −90° C. to 50° C., preferably −10° C. to 30° C., to synthesize an α-amino-α',α'-dihaloketone derivative of the formula (3).

The α-amino acid constituting said α-amino acid ester derivative of the formula (1) is not particularly restricted but includes phenylalanine, alanine, valine, leucine, isoleucine and phenylglycine, among others. Preferred is phenylalanine or phenylglycine. In the present invention, even when an optically active amino acid is used as the starting compound, the desired compound can be obtained without decreasing in optical activity. Therefore, more preferred amino acid is L-phenylalanine or L-phenylglycine, which is optically active.

The base mentioned above is not particularly restricted but includes alkyllithiums, alkylmagnesium halides, lithium amides, e.g. lithium diisopropylamide, lithium hexamethyldisilazide, etc., and halomagnesium dialkylamides which can be prepared by reacting a Grignard reagent with a secondary amine, e.g. chloromagnesium diisopropylamide, bromomagnesium diisopropylamide and chloromagnesium dicyclohexylamide. These bases can be used independently or in a combination of 2 or more species. Preferred bases are halomagnesium dialkylamides, and particularly preferred base is chloromagnesium diisopropylamide. The amount of use of said base is 2 to 10 molar equivalents, preferably 3 to 5 molar equivalents, based on the α-amino acid ester derivative.

The dihalomethane of the formula (2) is not particularly restricted but includes dichloromethane, dibromomethane and bromochloromethane, among others. Preferred is dibromomethane. The amount of use of said dihalomethane is 1 to 10 molar equivalents, preferably 1 to 3 molar equivalents, based on the α-amino acid ester derivative.

The reaction solvent for use in conducting this reaction is not particularly restricted but includes ether solvents, such as diethyl ether, 1,2-dimethoxyethane, t-butyl methyl ether, tetrahydrofuran, etc.; aliphatic hydrocarbon solvents, such as hexane, pentane, etc.; and aromatic hydrocarbon solvents, such as benzene, toluene and so forth. These solvents can be used independently or in a combination of 2 or more species.

This reaction is carried out by diluting said α-amino acid ester derivative and dihalomethane with the reaction solvent, then adding the base to the dilution at −90° C. to 50° C., preferably −10° C. to 30° C., and stirring the mixture for 1 to 24 hours, preferably 2 to 10 hours.

The after-treatment following the reaction comprises stopping the reaction by adding the reaction mixture to diluted hydrochloric acid, diluted sulfuric acid or an aqueous solution of ammonium chloride or the like, extracting the mixture with a suitable solvent such as ethyl acetate, diethyl ether and toluene, washing the extract serially with saturated aqueous solution of sodium hydrogencarbamate, saturated aqueous solution of sodium chloride, water and the like, followed by concentration and the routine purification procedure, e.g. recrystallization, column chromatography or the like, whereby the α-amino-α',α'-dihaloketone can be isolated.

Among the α-amino-α',α'-dihaloketone derivatives of the formula (3) which can be obtained by the above reaction, the derivatives of the formula (3) wherein $R^1$ represents abenzyl group, $X^1$ represents a bromine atom and $X^2$ represents a chlorine atom or a bromine atom are novel compounds which have not been described in the literatures.

The process for producing a β-amino acid ester derivative from an α-amino-α',α'-dihaloketone is now described.

Thus, the α-amino-α',α'-derivative of the formula (3) is reacted with a lithium amide and an alkyllithium in the order mentioned and the reaction product is treated with an acid in an alcohol to give the objective β-amino acid ester derivative of the formula (4) In accordance with this reaction, even when the α-amino-α',α'-dihaloketone derivative is an optically active compound, the objective compound can be produced without decreasing in optical activity.

The lithium amide mentioned above is not particularly restricted but includes lithium hexamethyldisilazide, lithium diisopropylamide and lithium dicyclohexylamide, among others. Preferred is lithium hexamethyldisilazide or lithium diisopropylamide. The amount of use is 2 to 5 molar equivalents, preferably 2 to 3 molar equivalents, based on the α-amino-α',α'-dihaloketone derivative.

The alkyllithium mentioned above is not particularly restricted but includes methyllithium, phenyllithium, n-butyllithium, sec-butyllithium, t-butyllithium, and n-hexyllithium, among others. Preferred is n-butyllithium. The amount of use is 1 to 10 molar equivalents, preferably 2 to 5 molar equivalents, relative to the α-amino-α',α'-dihaloketone derivative.

The reaction solvent for use in conducting this reaction is not particularly restricted but includes ether solvents, such as diethyl ether, 1,2-dimethoxyethane, t-butyl methyl ether, tetrahydrofuran, etc.; aliphatic hydrocarbon solvents, such as hexane, pentane, etc.; and aromatic hydrocarbon solvents, such as benzene, toluene and so forth. These can be used independently or two or more of them can be used in combination.

The alcohol mentioned above is not particularly restricted but includes lower alcohols such as methanol, ethanol, n-propyl alcohol, etc. Preferred is methanol or ethanol. The alkyl moiety of this alcohol corresponds to $R^3$ in the formula (4).

The acid for use in the above treatment is not particularly restricted but hydrogen chloride and sulfuric acid can be mentioned as preferred examples.

This reaction is carried out be reacting an α-amino-α',α'-dihaloketone of the formula (2) with said lithium amide at −90° C. to 20° C., preferably −80° C. to 50° C., for 10 minutes to 180 minutes, preferably 30 to 60 minutes, and then reacting it with said alkyllithium at −90° C. to 20° C., preferably −80° C. to −50° C., for 10 to 180 minutes, preferably 30 to 60 minutes, and adding the reaction mixture to an alcohol containing said acid.

The after-treatment may for example comprise adding water to stop the reaction, extracting the mixture with a solvent such as ethyl acetate, diethyl ether, toluene or the like, washing the extract with saturated aqueous solution of sodium hydrogencarbonate, saturated aqueous solution of sodium chloride, water and the like, followed by concentration and isolation by the routine procedure such as recrystallization, chromatography and/or the like, whereby the β-amino acid ester derivative can be isolated.

As an alternative, the β-amino acid ester derivative of the formula (4) can be directly obtained by reacting an α-amino acid ester derivative of the formula (1) with a dihalomethane of the formula (2) and a base in the same manner as above to synthesize an α-amino-α',α'-dihaloketone of the formula (3) and, without quenching the reaction, reacting it further with said lithium amide and alkyllithium in succession, followed by said acid treatment in an alcohol.

BEST MODE FOR CARRYING OUT THE INVENTION

The following examples illustrate the present invention in further detail without defining the scope of the invention.

EXAMPLE 1

Production of tert-butyl (S)-(1-benzyl-3,3-dibromo-2-oxopropyl)carbamate

Under nitrogen gas, a solution of diisopropylamine (2.4 g, 21.6 mmol) in tetrahydrofuran (10 mL) was added to n-butyllithium (in 1.6 M hexane, 13.5 mL, 21.6 mmol) at 5° C. and the mixture was stirred for 30 minutes (liquor A). Separately, under nitrogen gas in another vessel, a solution was prepared from methyl (S)-2-tert-butyloxycarbonylamino-3-phenylpropanoate (2.0 g, 7.2 mmol), dibromomethane (2.5 g, 14.4 mmol) and tetrahydrofuran (10 mL) and cooled to −70° C. (liquor B). To this liquor B was added said liquor A over 30 minutes at −70° C., and the mixture was stirred for 30 minutes at the same temperature and then warmed to 20° C. This reaction mixture was poured in 25 mL of 2N-HCl for hydrolysis and, then, extracted with 10 mL of ethyl acetate. The organic layer was washed with 20 mL of water, dried over anhydrous magnesium sulfate, and concentrated under reduced pressure to recover 2.670 g of black solid. This solid was recrystallized from ethyl acetate/hexane to provide brown crystals of tert-butyl (S)-(1-benzyl-3,3-dibromo-2-oxopropyl)carbamate (630 mg, 92.2 area %, yield 19%).

$^1$H-NMR (400 MHz, CDCl$_3$) δ: 1.40 (s, 9H), 3.05 (dd, 1H), 3.17 (dd, 1H), 4.91 (m, 1H), 4.98 (m, 1H), 6.00 (s, 1H), 7.13–7.36 (m, 5H).

EXAMPLE 2

Production of tert-butyl (S)-(1-benzyl-3,3-dibromo-2-oxopropyl)carbamate

Under nitrogen gas, diisopropylamine (17.4 g, 157.5 mmol) was added to n-butylmagnesium chloride (1.8 mol/kg, 79.6 g, 143.2 mmol) over 30 minutes at 40° C. and the mixture was further stirred for 2 hours at the same temperature to prepare a white slurry (liquor A). Separately, under nitrogen gas in another vessel, a solution was prepared from methyl (S)-2-tert-butyloxycarbonylamino-3-phenylpropanoate (10.0 g, 35.8 mmol), dibromomethane (12.45 g, 71.6 mmol) and THF (20 mL) (liquor B). To this liquor B was added said liquor A over 1 hour at an internal temperature of about 5° C., and the reaction was further conducted for 1 hour. This reaction mixture was poured in a mixture of concentrated hydrochloric acid (34.5 g), water (50 g) and ethyl acetate (100 mL) over 15 minutes for hydrolysis. After phase separation, the organic layer was washed with 2 portions of water (50 mL) and partially concentrated and the residue was precipitated from hexane to provide white crystals of tert-butyl (S)-(1-benzyl-3,3-dibromo-2-oxo-propyl)carbamate (8.709 g, 95.5 area %, yield 55%).

EXAMPLE 3

Production of benzyl (S)-(1-benzyl-3,3-dibromo-2-oxopropyl)carbamate

Under nitrogen gas, diisopropylamine (38.8 g, 383.4 mmol) was added to n-butylmagnesiumchloride (1.8 mol/kg, 178 g, 319.5 mmol) over 30 minutes at 40° C. and the mixture was further stirred for 2 hours at the same temperature to prepare a white slurry (liquor A). Separately, under nitrogen gas was in another vessel, a solution was prepared from methyl (S)-2-benzyloxycarbonylamino-3-phenylpropanoate (20.0 g, 63.9 mmol), dibromomethane (22.22 g, 127.8 mmol) and THF (40 mL) (liquor B). To this liquor B was added said liquor A over 2 hours at an internal temperature of about 5° C., and the reaction was further conducted at 5° C. for 2 hours. This reaction mixture was poured in a mixture of concentrated hydrochloric acid (73.3 g), water (100 g) and ethyl acetate (50 mL) over 1 hour for hydrolysis. After phase separation, the organic layer was washed with 2 portions of water (100 mL each). The organic layer was concentrated under reduced pressure to recover 34.38 g of black oil. This oil was purified by silica gel column chromatography to recover 22.34 g of yellow crude crystals. This crystal crop was recrystallized from ethyl acetate/hexane to provide white crystals of benzyl (S)-(1-benzyl-3,3-dibromo-2-oxopropyl)carbamate (11.99 g, 88.0 area %, yield 57%).

$^1$H-NMR (400 MHz, CDCl$_3$) δ: 3.07 (dd, 1H), 3.16 (dd, 1H), 5.00 (m, 1H), 5.07 (d, 2H), 5.32 (d, 1H), 5.93 (s, 1H), 7.10–7.47 (m, 10H)

EXAMPLE 4

Production of ethyl (S)-(1-benzyl-3,3-dibromo-2-oxopropyl)carbamate

Under nitrogen gas, diisopropylamine (9.67 g, 95.52 mmol) was added to n-butyl magnesium chloride (1.8mol/kg, 44.2 g, 79.6 mmol) over 30 minutes at 40° C. and the mixture was further stirred for 2 hours at the same temperature to prepare a white slurry (liquor A). Separately, under nitrogen gas in another vessel, a solution was prepared from methyl (S)-2-ethyloxycarbonylamino-3-phenylpropanoate (5.0 g, 19.9 mmol), dichloromethane (3.38 g, 39.8 mmol) and THF (20 g) (liquor B) To this liquor B was added said liquor A over 1 hour at an internal temperature of about 5° C., and the reaction was further conducted at 5° C. for 1 hour and at 20° C. for 15 hours. This reaction mixture was poured in a mixture of concentrated hydrochloric acid (18.26 g), water (50 g) and ethyl acetate (30 mL) over 15 minutes for hydrolysis. After phase separation, the organic layer was washed with 2 portions of water (50 mL each) and under reduced pressure to give 6.259 g of black oil. This oil was precipitated from ethyl acetate/hexane to provide yellow crystals of ethyl (S)-(1-benzyl-3,3-dibromo-2-oxopropyl)carbamate (989 mg, 91.4 area %, yield 15%).

$^1$H-NMR (400 MHz, CDCl$_3$) δ: 1.21 (t, 3H), 3.04 (m, 1H), 3.21 (dd, 1H), 4.09 (q, 2H), 4.95 (m, 1H), 5.14 (m, 1H), 6.05 (s, 1H), 7.10–7.42 (m, 5H)

EXAMPLE 5

Production of tert-butyl (S)-(1-benzyl-3-bromo-3-chloro-2-oxopropyl)carbamate

Under nitrogen gas, diisopropylamine (19.92 g, 196.9 mmol) was added to n-butylmagnesium chloride (1.8 mol/kg, 99.4 g, 179 mmol) over 30 minutes at 40° C. and the mixture was further stirred for 2 hours at the same temperature to prepare a white slurry (liquor A). Separately, under nitrogen gas in another vessel, a solution was prepared from methyl (S)-2-tert-butyloxycarbonylamino-3-phenylpropanoate (10.0 g, 35.8 mmol), bromochloromethane (9.27 g, 71.6 mmol) and THF (20 g) (liquor B). To this liquor B was added said liquor A over 1.5 hours at an internal temperature of about 5° C., and the reaction was conducted at 5° C. for 1 hour and at 20° C. for 16 hours. This reaction mixture was poured in a mixture of concentrated hydrochloric acid (43.12 g), water (100 g) and ethyl acetate (50 mL) over 10 minutes for hydrolysis. After phase separation, the organic layer was washed serially with water (100 mL) and saturated NaCl/H$_2$O, dried over anhydrous magnesium sulfate, and concentrated under reduced pressure to recover 20.08 g of a reddish brown solid. This solid was recrystallized from ethyl acetate/hexane to provide yellow crystals of tert-butyl (S)-(1-benzyl-3-bromo-3-chloro-2-oxopropyl)carbamate (4.409 mg, 90.7 area %, yield 30%, diastereomer ratio=42/58) as a mixture of diastereomers.

$^1$H-NMR (400 MHz, CDCl$_3$) δ: 1.39 (s, 9H), 1.41 (s, 9H), 2.92–3.30 (m, 2H+2H), 4.75–5.08 (m, 2H+2H), 5.89 (S, 1H), 6.29 (s, 1H), 7.17–7.42 (m, 5H+5H)

EXAMPLE 6

Production of tert-butyl (S)-(1-benzyl-3,3-dichloro-2-oxopropyl)carbamate

Under nitrogen gas, diisopropylamine (19.92 g, 196.9 mmol) was added to n-butylmagnesium chloride (1.8 mol/kg, 99.4 g, 179 mmol) over 30 minutes at 40° C. and the mixture was further stirred for 2 hours at the same temperature to prepare a white slurry (liquor A). Separately, under nitrogen gas in another vessel, a solution was prepared from methyl (S)-2-tert-butyloxycarbonylamino-3-phenylpropanoate (10.0 g, 35.8 mmol), dichloromethane (6.09 g, 71.6 mmol) and THF (20 g) (liquor B). To this liquor B was added said liquor A over 1.5 hours at an internal temperature of about 5° C., and the reaction was conducted at 5° C. for 6 hours and at 20° C. for 16 hours. This reaction mixture was poured in a mixture of concentrated hydrochloric acid (43.12 g), water (100 g) and ethyl acetate (50 mL) over 10 minutes for hydrolysis. After phase separation, the organic layer was washed serially with water (100 mL) and saturated sodium hydrogencarbonate/H$_2$O, dried over anhydrous magnesium sulfate, and concentrated under reduced pressure to recover 20.22 g of a reddish brown solid. This solid was recrystallized from ethyl acetate/hexane to provide yellow crystals of tert-butyl (S)-(1-benzyl-3,3-dichloro-2-oxopropyl)carbamate (3.921 g, 98.1 area %, yield 32%).

$^1$H-NMR (400 MHz, CDCl$_3$) δ: 1.40 (s, 9H), 3.02 (dd, 1H), 3.21 (dd, 1H), 4.82–4.91 (m, 1H), 4.92–5.01 (m, 1H), 6.09 (s, 1H), 7.18–7.35 (m, 5H)

EXAMPLE 7

Production of benzyl (S)-(1-phenyl-3,3-dibromo-2-oxopropyl)carbamate

Under nitrogen gas, diisopropylamine (27.9 g, 275.9 mmol) was added to n-butylmagnesium chloride (1.8 mol/kg, 139.4 g, 250.9 mmol) over 30 minutes at 40° C. and the mixture was further stirred for 2 hours at the same temperature to prepare a white slurry (liquor A). Separately, under nitrogen gas in another vessel, a solution was prepared from methyl (S)-2-benzyloxycarbonylamino-2-phenylpropionate (30.0 g, 50.17 mmol), dibromomethane (17.44 g, 100.3 mmol) and THF (30 g) (liquor B). To this liquor B was added liquor A over 1 hour at an internal temperature of about 5° C., and the reaction was further conducted at 5° C. for 1 hour. This reaction mixture was poured in a mixture of concentrated hydrochloric acid (60.43 g), water (100 g) and ethyl acetate (100 mL) over 30 minutes for hydrolysis. After phase separation, the organic layer was washed with 2 portions of water (100 mL each), dried over anhydrous magnesium sulfate, and concentrated under reduced pressure to give 25.44 g of a black oil. This oil was purified by silica gel column chromatography to provide a red oil of benzyl (S)-(1-phenyl-3,3-dibromo-2-oxopropyl)carbamate (17.15 g, 68.6 area %, yield 39%).

$^1$H-NMR (400 MHz, CDCl$_3$) δ: 5.08 (dd, 2H), 5.95 (bs, 2H), 7.25 (s, 1H), 7.19–7.49 (m, 10H)

EXAMPLE 8

Production of tert-butyl (R)-(1-benzyl-3,3-dibromo-2-oxopropyl)carbamate

Under nitrogen gas, diisopropylamine (21.5 g, 212.7 mmol) was added to n-butylmagnesium chloride (1.8 mol/kg, 104 g, 193.4 mmol) over 30 minutes at 40° C. and the mixture was further stirred for 2 hours at the same temperature to prepare a white slurry (liquor A). Separately, under nitrogen gas in another vessel, a solution was prepared from methyl (R)-2-tert-butyloxycarbonylamino-3-phenylpropanoate (purity 76.3 wt. %, 14.14 g, 38.67 mmol), dibromomethane (13.44 g, 77.3 mmol) and THF (20 g) (liquor B). To this liquor B was added liquor A over 1 hour at an internal temperature of about 5° C., and the reaction was further conducted at 5° C. for 1 hour. Then, this reaction mixture and concentrated hydrochloric acid (46.6 g) were concurrently added to a solution composed of water (50 g) and ethyl acetate (100 mL) and the hydrolysis was carried out for 30 minutes, during which time the reaction system was controlled at pH 1 to 7. After phase separation, the organic layer was washed with 2 portions of saturated sodium chloride/H$_2$O (100 mL each), dried over anhydrous magnesium sulfate, and concentrated under reduced pressure to give 30.6 g of a black oil. HPLC assay showed that the objective tert-butyl (R)-(1-benzyl-3,3-dibromo-2-oxopropyl)carbamate had been produced in a yield of 61%. This crystal crop was recrystallized from ethyl acetate/hexane to provide yellow crystals of tert-butyl (R)-(1-benzyl-3,3-dibromo-2-oxopropyl)carbamate (9.033 g, 90.4 area %, yield 50%).

HPLC (Daicel Chiral Cell AD) analysis of the above product showed that the optical purity was 98.6% e.e. for the crude product and 99.4% e.e. for the pure crystal.

EXAMPLE 9

Production of methyl (S)-3-tert-butyloxycarbonylamino-4-phenylbutanoate

Under nitrogen, a solution composed of hexamethyldisilazane (1.53 g, 9.5 mmol) and THF (5 mL) was added to n-butyllithium (1.6 M, 5.9 mL, 9.5 mmol) at 5° C. and the mixture was stirred for 30 minutes (liquor A). Separately, under nitrogen in another vessel, a solution was prepared from tert-butyl (S)-(1-benzyl-3,3-dibromo-2-oxopropyl)carbamate (2.0 g, 4.75 mmol) obtained by the procedure in Example 1 and THF (20 mL) (liquor B). To liquor B was added liquor A over 10 minutes at −70° C., followed by stirring at the same temperature for 30 minutes (liquor C). Then, n-butyllithium (1.6 M, 14.8 mL, 23.75 mmol) was added dropwise over 10 minutes at −70 ° C. and the whole mixture was further stirred for 30 minutes. Thereafter, this liquor C was poured in a solution composed of methanol (30 mL) and concentrated sulfuric acid (1.02 g) at 5° C. and, after 30 minutes of stirring, a saturated aqueous solution of sodium hydrogencarbonate (50 mL) was added for hydrolysis. This reaction mixture was extracted with ethyl acetate (50 mL) and the extract was dried over anhydrous magnesium sulfate and concentrated under reduced pressure to give 2.18 g of a yellow oil. This oil was purified by silica gel column chromatography to provide a yellow oil of methyl (S)-3-tert-butyloxycarbonylamino-4-phenylbutanoate (633 mg, 97.5 area %, yield 44%).

$^1$H-NMR (400 MHz, CDCl$_3$) δ: 1.41 (s, 9H), 2.47 (dd, 1H), 2.51 (dd, 1H), 2.79 (dd, 1H), 2.82 (dd, 1H), 3.68 (s, 3H), 4.13 (m, 1H), 5.06 (bs, 1H), 7.15–7.32 (m, 5H)

EXAMPLE 10

Production of methyl (R)-3-tert-butyloxycarbonylamino-4-phenylbutanoate

Under nitrogen, a solution composed of hexamethyldisilazane (1.38 g, 8.58 mmol) and THF (5 mL) was added to n-butyllithium (1.6 M, 5.4 mL, 8.58 mmol) at 5° C. and the mixture was stirred for 30 minutes (liquor A). Separately, under nitrogen gas in another vessel, a solution was prepared from the tert-butyl (R)-(1-benzyl-3,3-dibromo-2-oxopropyl)carbamate obtained by the procedure in Example 8 (2.0 g, 4.29 mmol) and THF (10 mL) (liquor B). To liquor B was added liquor A over 10 minutes at −70° C., followed by stirring at the same temperature for 30 minutes (liquor C). Then, n-butyllithium (1.6M, 8.0 mL, 12.87 mmol) was added dropwise over 10 minutes at −70° C. and the whole mixture was further stirred for 1 hour. This liquor C was then poured in a solution composed of methanol (10 mL) and concentrated sulfuric acid (1.26 g) at 5° C. and, after 30 minutes of stirring, water (50 mL) was added for hydrolysis. This reaction mixture was extracted with ethyl acetate (50 mL) and the extract was dried over anhydrous magnesium sulfate and concentrated under reduced pressure to give 2.30 g of a yellow oil. HPLC assay of the oil showed that the objective methyl (R)-3-tert-butyloxycarbonylamino-4-phenylbutanoate had been produced in a yield of 62%. The optical purity as determined by HPLC (Daicel Chiral Cell AD) was 100% e.e. for the crude product.

EXAMPLE 11

Production of methyl (S)-3-tert-butyloxycarbonylamino-4-phenylbutanoate

Under nitrogen, t-butylmagnesium chloride (1.8 M, 2.64 mL, 4.76 mmol) was added to a solution composed of tert-butyl (S)-(1-benzyl-3,3-dibromo-2-oxopropyl)carbamate (1.0 g, 2.38 mmol) obtained by the procedure in Example 1 and THF (10 mL) at 5° C. and the mixture was stirred for 30 minutes. Then, n-butyllithium (1.6 M, 4.5 mL, 7.14 mmol) was further added dropwise over 10 minutes at 5° C. and the whole mixture was stirred for another 2 hours (liquor A). This liquor A was poured in a solution composed of methanol (10 mL) and concentrated sulfuric acid (641 mg) at 5° C. and the mixture was stirred for 30 minutes. HPLC assay revealed that the objective methyl (S)-3-tert-butyloxycarbonylamino-4-phenylbutanoate had been produced in a yield of 23%.

EXAMPLE 12

Production of methyl (S)-3-tert-butyloxycarbonylamino-4-phenylbutanoate

Under nitrogen gas, t-butylmagnesium chloride (1.8 M, 2.64 mL, 4.76 mmol) was added to solution composed of tert-butyl (S)-(1-benzyl-3,3-dibromo-2-oxopropyl)carbamate (1.0 g, 2.38 mmol) obtained by the procedure in Example 1 and THF (10 mL), at 5° C. and the mixture was stirred for 30 minutes. Then, n-butylmagnesium chloride (1.8M, 4.0 mL, 7.14 mmol) was further added dropwise over 10 minutes at 5° C. After the temperature had risen to 20° C., the mixture was stirred for 16 hours (liquor A). This liquor A was added to a solution composed of methanol (10 mL) and concentrated sulfuric acid (641 mg) at 5° C., followed by stirring for 30 minutes. HPLC assay revealed that the objective methyl (S)-3-tert-butyloxycarbonylamino-4-phenylbutanoate had been produced in a yield of 9%.

EXAMPLE 13

Production of methyl (S)-3-tert-butyloxycarbonylamino-4-phenylbutanoate

Under nitrogen, a solution of hexamethyldisilazane (1.16 g, 7.2 mmol) in THF (5 mL) was added to n-butyllithium (1.6 M, 4.5 mL, 7.2 mmol) at 5° C. and the mixture was stirred for 30 minutes (liquor A). Separately, under nitrogen gas in another vessel, a solution was prepared from tert-butyl (S)-(1-benzyl-3-bromo-3-chloro-2-oxopropyl)carbamate (1.25 g, 3.0 mmol) obtained by the procedure in Example 5 and THF (10 mL) (liquor B). To this liquor B was added liquor A over 1 minute at −70° C., and the mixture was stirred at the same temperature for 30 minutes (liquor C). Then, n-butyllithium (1.6 M, 9.4 mL, 15.0 mmol) was further added dropwise over 1 minute at −70° C., followed by stirring for 2 hours. This liquor was added to a solution composed of methanol (20 mL) and concentrated sulfuric acid (1.76 g) at 5° C. and the mixture was stirred for 30 minutes. HPLC analysis revealed that the objective methyl (S)-3-tert-butyloxycarbonylamino-4-phenylbutanoate had been produced in a yield of 41%.

EXAMPLE 14

Production of methyl (S)-3-tert-butyloxycarbonylamino-4-phenylbutanoate

Under nitrogen, a solution composed of hexamethyldisilazane (1.16 g, 7.2 mmol) and THF (5 mL) was added to n-butyllithium (1.6 M, 4.5 mL, 7.2 mmol) at 5° C. and the mixture was stirred for 30 minutes (liquor A). Separately, under nitrogen gas in another vessel, a solution was prepared from the tert-butyl (S)-(1-benzyl-3,3-dichloro-2-oxopropyl)carbamate (1.02 g, 3.0 mmol) obtained by the procedure in Example 6 and THF (10 mL) (liquor B). To this liquor B was added liquor A over 1 minute at −70° C., and the mixture was stirred at the same temperature for 30 minutes (liquor C). Then, n-butyllithium (1.6 M, 9.4 mL, 15.0 mmol) was further added dropwise over 1 minute at −70° C., followed by stirring at the same temperature for 1 hour. After the temperature had risen to 20° C., the mixture was further stirred for 3 days. This liquor was added to a solution composed of methanol (20 mL) and concentrated sulfuric acid (1.76 g) at 5° C. and the mixture was stirred for 30 minutes. HPLC assay revealed that the objective methyl (S)-3-tert-butyloxycarbonylamino-4-phenylbutanoate had been produced in a yield of 4%.

EXAMPLE 15

Production of ethyl (S)-3-benzyloxycarbonylamino-4-phenylbutanoate

Under nitrogen, a solution composed of hexamethyldisilazane (1.25 g, 7.74 mmol) and THF (10 mL) was added to n-butyllithium (1.6 M, 4.8 mL, 7.74 mmol) at 5° C. and the mixture was stirred for 30 minutes (liquor A). Separately, under nitrogen gas in another vessel, a solution was prepared from the benzyl (S)-(1-benzyl-3,3-dibromo-2-oxopropyl)carbamate (2.0 g, 3.87 mmol) obtained by the procedure in Example 3 and THF (20 mL) (liquor B). To this liquor B was added liquor A over 10 minutes at −70° C., and the mixture was stirred at the same temperature for 20 minutes (liquor C). Then, n-butyllithium (1.6 M, 12.1 mL, 19.35 mmol) was further added dropwise over 30 minutes at −70° C., followed by stirring for 30 minutes. The liquor C was added to a solution composed of ethanol (30 mL) and concentrated sulfuric acid (1.88 g) at 5° C. and the mixture was stirred for 30 minutes. This liquor was diluted with water (50 mL) and extracted with ethyl acetate (50 mL). The extract was washed with 50 mL of water, dried over anhydrous magnesium sulfate, and concentrated under reduced pressure to give 1.94 g of an orange-colored oil. This oil was purified by silica gel column chromatography to provide a light-yellow oil of ethyl (S)-3-benzyloxycarbonylamino-4-phenylbutanoate (822 mg, 95.1 area %, yield 59%).

$^1$H-NMR (400 MHz, CDCl$_3$) δ: 1.23 (t, 3H), 2.40–2.57 (m, 2H), 2.79–3.00 (m, 2H), 4.13 (q, 2H), 4.22 (m, 1H), 5.06 (s, 2H), 5.33 (d, 1H), 7.08–7.43 (m, 10H)

EXAMPLE 16

Production of methyl (S)-3-benzyloxycarbonylamino-3-phenylpropionate

Under nitrogen, a solution composed of hexamethyldisilazane (9.49 g, 58.8 mmol) and THF (50 mL) was added to n-butyllithium (1.6 M, 36.8 mL, 58.8 mmol) at 5° C. over 30 minutes and the mixture was further stirred for 30 minutes (liquor A). Separately, under nitrogen gas in another vessel, a solution was prepared from the benzyl (S)-(1-phenyl-3,3-dibromo-2-oxopropyl)carbamate (12.6 g, 19.6 mmol) obtained by the procedure in Example 7 and THF (16.2 g) (liquor B). To this liquor B was added liquor A over 30 minutes at −70° C., and the mixture was stirred at the same temperature for 30 minutes (liquor C). Then, n-butyllithium (1.6 M, 61.3 mL, 294 mmol) was further added dropwise over 30 minutes at −70° C., followed by stirring for 30 minutes. This liquor was added to a solution composed of methanol (50 mL) and concentrated sulfuric acid (11.52 g) at −70° C. After the temperature had risen to 20° C., the mixture was stirred for 30 minutes. This reaction mixture was diluted with 100 mL of water and the organic layer was taken and washed serially with water (50 mL), saturated sodium hdyrogencarbonate/H$_2$O (50 mL) and water (50 mL), and dried over anhydrous magnesium sulfate. It was then concentrated under reduced pressure to give 10.28 g of a red oil. This oil was purified by silica gel column chromatography to provide a yellow oil of methyl (S)-3-benzyloxycarbonylamino-3-phenylpropionate (2.896 g, 80.0 area %, yield 42%).

$^1$H-NMR (400 MHz, CDCl$_3$) δ: 2.75–2.94 (m, 2H), 3.58 (s, 3H), 5.08 (dd, 2H), 5.27 (m, 1H), 5.80 (bs, 1H), 7.15–7.42 (m, 10H)

EXAMPLE 17

Production of methyl (S)-3-tert-butyloxycarbonylamino-4-phenylbutanoate

Under nitrogen gas, diisopropylamine (9.06 g, 89.5 mmol) was added to n-butylmagnesium chloride (1.8 M, 44.8 mL, 80.6 mmol) over 30 minutes at 40° C. and the mixture was further stirred at the same temperature for 2 hours, whereby a white slurry was obtained (liquor A). Separately, under nitrogen gas in another vessel, a solution was prepared from methyl (S)-2-tert-butyloxycarbonylamino-3-phenylpropanoate (5.0 g, 17.9 mmol), dibromomethane (4.67 g, 26.9 mmol) and THF (15 g) (liquor B). To this liquor B was added liquor A over 1 hour at an internal temperature of about 5° C., and the reaction was further conducted for 1 hour. Then, n-butyllithium (1.6 M, 55.9 mL, 89.5 mmol) was added dropwise over 1 hour at −70° C., followed by stirring at the same temperature for 30 minutes (liquor C). This liquor C was poured in a solution composed of methanol (50 mL) and concentrated sulfuric acid (17.5 g) at −70 ° C., and after the temperature had risen to 20° C., the mixture was stirred for 30 minutes. HPLC assay revealed that the objective methyl (S)-3-tert-butyloxycarbonylamino-4-phenylbutanate had been produced in a yield of 25%.

Industrial Applicability

The present invention, constituted as above, provides a process for producing an optically active β-amino acid ester derivative starting with a readily available optically active α-amino acid ester derivative, advantageously with good efficiency on a commercial scale and further provides an intermediate of value for the production of pharmaceuticals.

What is claimed is:

1. A process for producing an α-amino-α',α'-dihaloketone derivative of the following formula (3):

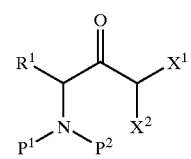

(3)

wherein R$^1$ represents a substituted or unsubstituted alkyl group containing 1 to 18 carbon atoms, an aralkyl group containing 7 to 18 carbon atoms or an aryl group containing 6 to 18 carbon atoms, P$^1$ represents a carbamate-form protecting group, P$^2$ represents a hydrogen atom, and X$^1$ and X$^2$ each independently represents a halogen atom, which comprises reacting an α-amino acid ester derivative of the following formula (1):

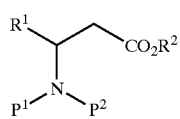

wherein $R^1$, $P^1$ and $P^2$ are as respectively defined above, $R^2$ represents an alkyl group containing 1 to 5 carbon atoms or an aralkyl group containing 7 to 12 carbon atoms with a base and a dihalomethane of the following formula (2):

$$CH_2X^1X^2 \qquad (2)$$

wherein $X^1$ and $X^2$ are as respectively defined above.

2. The process according to claim 1 wherein $X^1$ and $X^2$ each independently represents a chlorine atom or a bromine atom.

3. The process according to claim 1 wherein the base is a halomagnesium dialkylamide.

4. The process according to claim 1 wherein the dihalomethane of the formula (2) is dibromomethane and the base is chloromagnesium diisopropylamide.

5. The process according to claim 1, wherein
$R^1$ represents benzyl or phenyl,
$R^2$ represents methyl or ethyl,
$P^1$ represents t-butyloxycarbonyl, benzyloxycarbonyl, methyloxycarbonyl or ethyloxycarbonyl,
and $P^2$ represents hydrogen.

6. The process according to claim 1, wherein the α-amino acid ester derivative of the formula (1) is an optically active L-phenylalanine derivative or an optically active L-phenylglycine derivative.

7. The process according to claim 1, wherein the α-amino acid ester derivative of formula (1) is reacted with the base and the dihalomethane of the formula (2) at −10° C. to 30° C.

* * * * *

UNITED STATES PATENT AND TRADEMARK OFFICE
CERTIFICATE OF CORRECTION

PATENT NO. : 6,573,399 B1
DATED : June 3, 2003
INVENTOR(S) : Nishiyama et al.

It is certified that error appears in the above-identified patent and that said Letters Patent is hereby corrected as shown below:

Column 2,
Line 1, Formula (1) should read as follows:

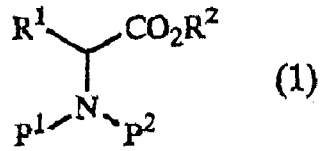

Column 13,
Line 1, Formula (1) should read as follows:

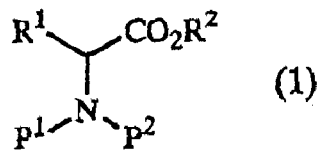

Signed and Sealed this

Twentieth Day of January, 2004

JON W. DUDAS
*Acting Director of the United States Patent and Trademark Office*